US006609423B1

(12) United States Patent
Retterath et al.

(10) Patent No.: US 6,609,423 B1
(45) Date of Patent: Aug. 26, 2003

(54) SYSTEM FOR CONTENT ANALYSIS OF COMESTIBLE PRODUCTS USING VOLUMETRIC DETERMINATION

(75) Inventors: James E. Retterath, Excelsior, MN (US); Robert A. Laumeyer, Minneapolis, MN (US); Steven A. Chapman, Eden Prairie, MN (US)

(73) Assignee: Facet Technology Corp., Eden Praire, MN (US)

( * ) Notice: Subject to any disclaimer, the term of this patent is extended or adjusted under 35 U.S.C. 154(b) by 0 days.

(21) Appl. No.: 10/226,640

(22) Filed: Aug. 23, 2002

(51) Int. Cl.⁷ ................................................. G01N 9/02
(52) U.S. Cl. ...................................................... 73/433
(58) Field of Search .......................... 73/866, 149, 433

(56) References Cited

U.S. PATENT DOCUMENTS

| | | |
|---|---|---|
| 3,282,115 A | 11/1966 | Taylor |
| 3,455,168 A | 7/1969 | Taylor et al. |
| 3,487,698 A | 1/1970 | Leger et al. |
| 4,184,371 A * | 1/1980 | Brachet ........................ 73/433 |
| 4,449,406 A | 5/1984 | van Haren |
| 4,813,101 A | 3/1989 | Brakels et al. |
| 5,077,477 A | 12/1991 | Stroman et al. |
| 5,105,825 A | 4/1992 | Dempster |
| 5,326,311 A | 7/1994 | Persoon et al. |
| 5,450,750 A | 9/1995 | Abler |

OTHER PUBLICATIONS

Website print-out: *Introduction to Sensors*, C.D.H. Williams, University of Exeter School of Physics, 9 pgs., Aug. 23, 2002.
Website print-out: *Pressure Sensors and Instruments*, http://www.globalspec.com, 1 pg., Aug. 23, 2002.
Website print-out: *Sensor Business Digest: Sensor Industry Developments and Trends*, Peter Adrian, Ed., 3 pgs., Sep. 1999.
Website print-out: *Pressure Transducers*, http://www.transicoil.com, 2 pgs., Aug. 23, 2002.
Website print-out: *Industrial Waste Water Monitoring*, http://www.alfadhlitrading.com, 5 pgs., Aug. 23, 2002.

* cited by examiner

Primary Examiner—Robert Raevis
(74) Attorney, Agent, or Firm—Patterson, Thuente, Skaar & Christensen, P.A.

(57) ABSTRACT

A system that performs content analysis on comestible products using volumetric determination with a single-chamber technique in a mass production environment. The content value determination system includes a conveyor system, a system for weighing the comestible products interposed along the path of the conveyor, a volumetric determination station that consists of a plurality of receiving chambers, and a control module. In this embodiment, each receiving chamber is equipped with a pressure sensor and a mechanical system for modifying the volume of the chamber. In addition, both the pressure sensors and the volume modification system of each receiving chamber are operably connected to the control module.

17 Claims, 2 Drawing Sheets

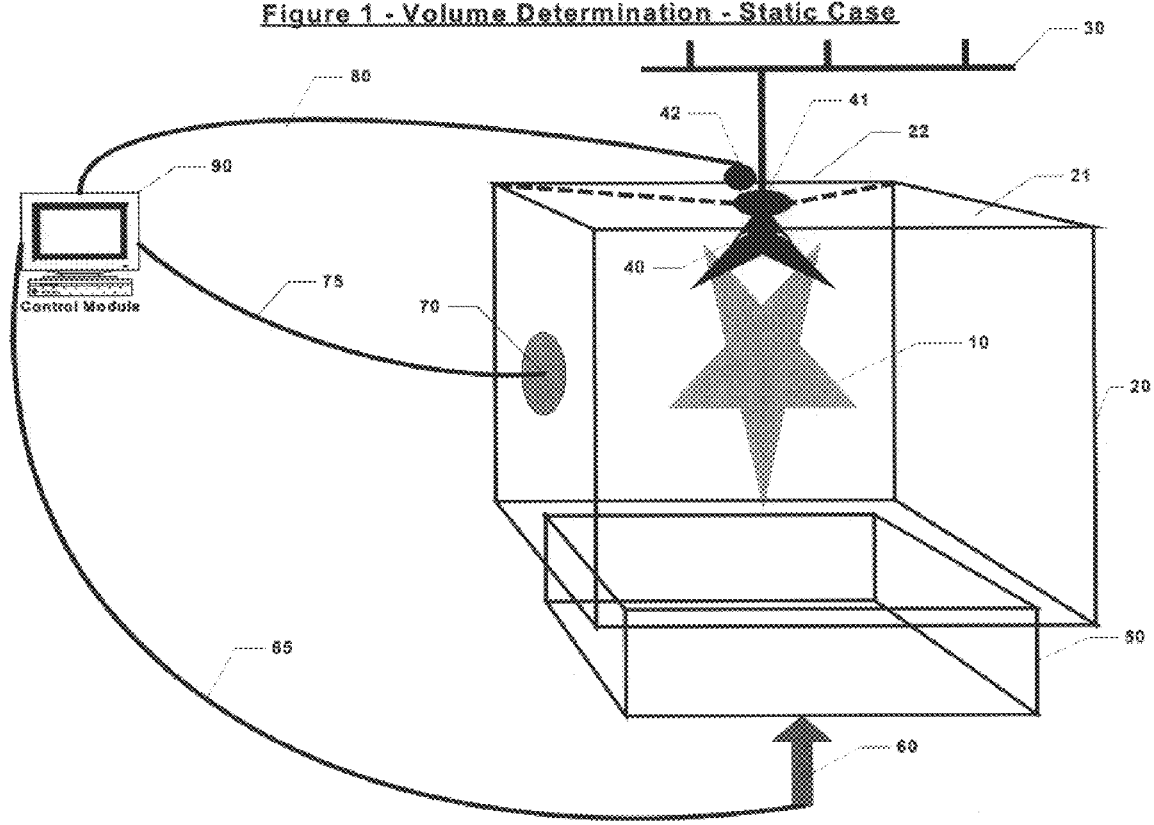

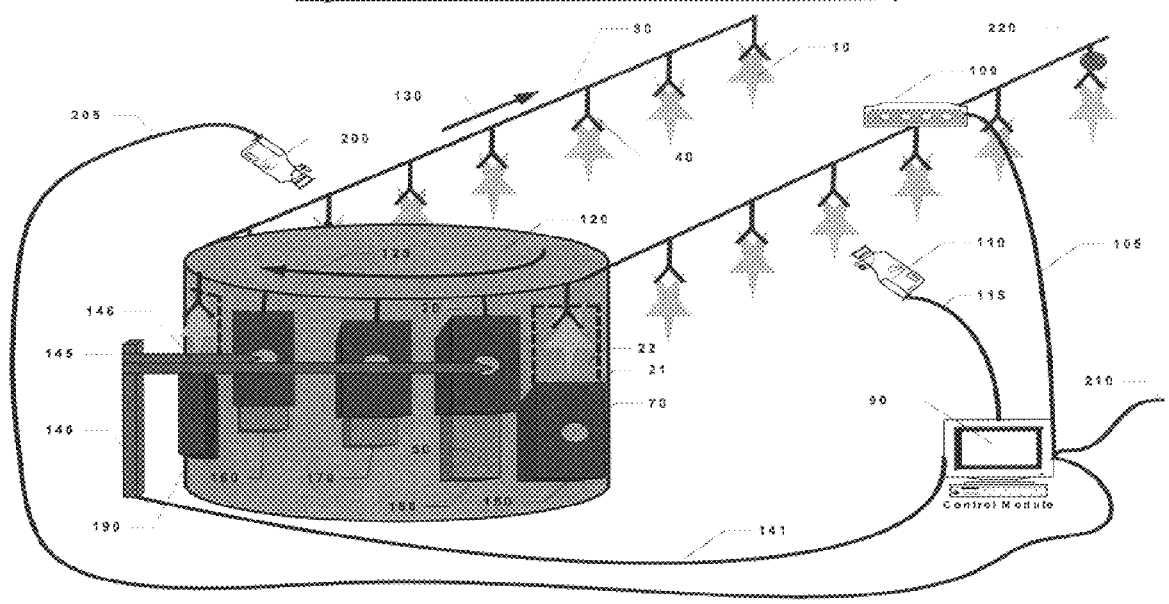

SYSTEM FOR CONTENT ANALYSIS OF COMESTIBLE PRODUCTS USING VOLUMETRIC DETERMINATION

FIELD OF THE INVENTION

The present invention is related to the field of volume determination of comestible products, i.e. meat cuts and whole animal carcasses. More specifically, the present invention is directed towards methods and devices for the automated high-speed volumetric determination of content values, including fat content, in various comestible products.

BACKGROUND OF THE INVENTION

Meat, poultry and fish producers are in the business of converting live animals into consumable products for humans. These producers experience thin profit margins and are constantly in search of processes that can increase the quality of the product offered to consumers.

One attribute that determines processed food quality is fat content. For most meat, poultry and fish products for example, reduced-fat cuts are more desirable and, as such, more profitable for the producers. Unfortunately, fat content for whole animal products or for processed animal parts is difficult to determine since most of the contained fat is not exposed at the surface of the whole animal carcass or processed cut. The industry needs a reliable way of determining fat content for processed meat, fish and poultry without subjecting the cut or carcass to destructive processes.

It is relatively easy to precisely measure the weight (and determine the mass) of meat, poultry and fish. Since fat and lean densities are well known in these industries, the percentage of fat content can be precisely determined if the exact volume of the cut or carcass could be measured. Unfortunately, the industry has not been able to realize a reliable approach for performing non-contact, non-destructive volumetric measurement, particularly in a mass production environment.

Previous methods for determining the fat content of cuts of meat required measuring the volume of the cuts of meat by compressing the tissue to a preselected state and directly measuring the volume. More specifically, these previous methods generally used a piston or a press plate to apply a substantial force to the meat sample in order to compact the meat sample and measure the volume. Examples are shown in U.S. Pat. No. 3,282,115 to Taylor et al.; U.S. Pat. No. 3,455,168 to Taylor et al.; U.S. Pat. No. 3,487,698 to Leger et al.; and U.S. Pat. No. 4,449,406 to van Haren. There are several drawbacks to these previous approaches for determining the volume of a meat sample. For example, the previous methods are time-consuming, are not well suited for modern automated food production facilities and do not provide a non-contact means for measuring the volume of the comestible product. In addition, these methods do not accurately measure the volume of every cut of meat, nor do they provide a means for determining the volume, and ultimately the fat content, of a whole animal carcass.

Another volumetric method for determining the fat content of an object consists of two connected chambers. In this method, the object to be measured is enclosed in the first chamber, which is connected to a second chamber of known volume. Pressure measurements are then made in the chamber housing the object both before and after a valve is opened connecting the two chambers. Knowing the two pressures and the incremental volume of the second chamber allows one to calculate the volume of the object in the first chamber by Boyle's law. Examples of these two chamber techniques are shown in U.S. Pat. No. 5,105,825 to Dempster and U.S. Pat. No. 5,450,750 to Abler.

While a two-chamber approach to volumetric measurement can be a useful way to compute the volume, and ultimately the fat content, of human subjects, this approach does not lend itself to the high-speed requirements of modern food processing facilities because of cost and space issues. The two-chamber approach is simply not feasible for mass production facilities because each measurement chamber requires a second connected chamber of known volume. With the large number of comestible products being produced, it would be desirable to provide an automated high-speed system for determining the volume, and ultimately the fat or other content values, of comestible products that addresses these and other shortcomings of the existing techniques.

SUMMARY OF THE INVENTION

The present invention is a system that performs content analysis on comestible products using volumetric determination with a single chamber technique in a mass production environment. The content value determination system includes a conveyor system, a system for weighing the comestible products interposed along the path of the conveyor, a volumetric determination station that consists of a plurality of receiving chambers, and a control module. In this embodiment, each receiving chamber is equipped with a pressure sensor and a mechanical system for modifying the volume of the chamber. In addition, both the pressure sensors and the volume modification system of each receiving chamber are operably connected to the control module.

In a preferred embodiment, the system includes an X-ray emitter and collector that provide X-ray images as the comestible products move along the path of the conveyor. The X-ray emitter and collector are operably connected to the control module, where the X-ray images are stored and used to determine the percentage of each comestible product that is bone material. This feature of the invention improves the overall accuracy of the content value determination for boned objects.

In another embodiment of the present invention, a volumetric determination device is provided. The volumetric determination device includes a single selectively sealable volumetric measurement chamber designed to enclose a comestible food product, such as a meat cut or whole animal carcass. The volumetric measurement chamber is equipped with a pressure sensor that is operably coupled to a control module. The pressure sensor measures the pressure inside the volumetric measurement chamber both before and after the volume inside the chamber has been modified by a known amount. A mechanical system is operably connected to the volumetric measurement chamber and provides a method for changing the volume of the chamber. In this embodiment, the volume of the comestible product can be computed by the control module based upon the initial pressure inside the chamber, the final pressure and the known change in volume of the chamber.

In a method in accordance with the present invention, a content value of a comestible product is determined by an automated process. The comestible products are placed onto a conveyor system. While moving along the conveyor system, the comestible products are weighed by a weighing system interposed along the path of the conveyor. The weighing system is operably connected to a control module, which records the weight of each comestible product. The conveyor system transports the comestible products to a volumetric determination station that consists of multiple receiving chambers. Each individual comestible product is encompassed in one of the receiving chambers and the initial pressure inside the chamber is recorded. The volume of the chamber is then modified by a known amount by a mechanical system and a second pressure is recorded. The control module, which is operably connected to each receiving chamber, then computes the volume of each of a plurality of comestible products based upon the change in pressure inside the chambers and the known modified volume. Once the volume of the comestible product is known, the control module can compute the fat content, or other content values, of the comestible product based upon the weight, volume and other characteristics of that product.

The present invention defines a process for determining the volume of any comestible product without exposing the product to fluids, chemicals, or heat. The invention utilizes the simple relationship between pressure and volume of a gas (commonly known as Boyle's Law and expressed as $P_1*V_1=P_2*V_2$) to compute the volume of a solid object. This method is especially useful in whole poultry production where the carcass cavity is mostly hidden from visual and other scanning methods.

In another embodiment of the invention, a method for determining percentage bone content in a comestible product is provided by subjecting the comestible product to non-visible radiation. An amount of absorbed non-visible radiation by the comestible product is detected and an internal image of at least one bone structure of the comestible product based upon the detected absorbed radiation is constructed. The image is transmitted to a control module that calculates a percentage of bone material in the comestible product based upon the internal image of the at least one bone structure.

The products referred to in this invention can be comestible products such as whole carcasses or cuts from carcasses of beef, pork, sheep, chickens, turkeys or fish. The object to be measured is placed in an airtight chamber of known volume. The pressure in the chamber is recorded upon closure of the chamber. The volume of the chamber is modified (preferably decreased) by a known amount with a piston, bellows, or some other high-speed mechanical or electromechanical device, and the resultant chamber pressure is recorded. These values can be used to determine the precise volume of the object in the chamber.

The objects described herein are primarily cuts and carcasses of beef, pork, poultry and fish. However, the same techniques can be used in other industries including, but not limited to, fruits, vegetables, grains and other processed foods. In fact, any industry that depends on high-volume manufacturing or processing that wishes to determine the content value of a particular ingredient of an intermediate or finished product can utilize the methods and devices of the present invention.

In contrast to previous methods for determining the volume of a meat cut which measured the volume of the meat cut directly, the present invention is capable of precisely measuring the volume of a whole animal carcass. This is accomplished primarily by designing volumetric measurement chambers that are able to accommodate either a cut of meat or an entire carcass. Furthermore, the present invention is designed to measure the volume of an object by utilizing only a single measurement chamber, thus eliminating the need to have a second measurement chamber attached to the first chamber.

BRIEF DESCRIPTION OF THE DRAWINGS

FIG. 1 depicts a diagram of the volumetric determination system for the static case.

FIG. 2 depicts a diagram of the fat content determination assembly.

DETAILED DESCRIPTION OF THE PREFERRED EMBODIMENTS

The following discussion assumes familiarity of one skilled in the art. Assume, for example, the initial pressure in a chamber is $P_1$, which occurs when the object to be measured is enclosed within the chamber. $P_1$ is probably the same pressure as the air outside the chamber, but this is not a necessary assumption for this invention. The volume in the chamber, which is precisely known, is denoted as $V_C$ and can be expressed as the sum of the volume of the object and the volume of the gas in the chamber.

$$V_C=V_O+V_G \qquad \text{(equation 1)}$$

Where:

$V_C$=volume of measurement chamber $V_O$=volume of object to be measured $V_G$=volume of gas in chamber This invention uses decreasing volume (which increases the pressure) to determine the volume of the gas in the chamber. The volume of the object, therefore, will be:

$$V_O=V_C-V_G \qquad \text{(equation 2)}$$

As gas in a space is decreased in volume, for example, the pressure within the space increases. This relationship of volume to pressure for a gas is known as Boyle's Law and can be expressed as:

$$P_1*V_1=P_2*V_2 \qquad \text{(equation 3)}$$

Where:

$P_1$=initial pressure of gas in chamber $P_2$=pressure of gas in chamber after volume is decreased $V_1$=original volume of gas in chamber $V_2$=final volume of gas in chamber There are two key factors not accounted for in equation 3—temperature and absorption. As a volume of gas is compressed, its temperature will rise. In addition, the cut of meat being measured will absorb some of the compressed gas. For a given volumetric measurement operation, all cuts of meat will be roughly the same size and will occur within equivalent amounts of time. Thus, the temperature increase of the gas and the absorption of the gas by the cut of meat will be roughly equivalent for all objects being measured. As such, it is possible to empirically determine a constant $K_V$ that can be used to modify equation 3 as:

$$P_1*V_1=K_V*P_2*V_2 \qquad \text{(equation 4)}$$

If a piston with a displacement of volume $V_P$ is utilized the final volume of the gas $V_2$ can be expressed as the initial volume $V_1$ less the piston displacement volume $V_P$.

$$V_2=V_1-V_P \qquad \text{(equation 5)}$$

Combining equations 4 and 5 and solving for $V_1$ yields:

$$V_1 = \frac{K_V * P_2 * V_P}{K_V * P_2 - P_1} \quad \text{(equation 6)}$$

Equating $V_1$ from equation 6 to $V_G$ in equation 2 yields the equation for the volume of the object being measured:

$$V_O = V_C - \frac{K_V * P_2 * V_P}{K_V * P_2 - P_1} \quad \text{(equation 7)}$$

Where $V_C$ is the volume of the chamber before the piston is engaged. One skilled in the art could modify equation 7 whereby the value of $V_C$ is the volume of the chamber after the piston is engaged.

Thus, to determine the volume of the object, the object is enclosed in an airtight chamber and the initial pressure $P_1$ is measured. A known modification in the volume of gas is introduced to the chamber, causing a change in gas pressure. The new pressure $P_2$ is measured. All values in equation 7 are known, so $V_O$ can be precisely computed.

This method works best when the volume of the object is a large percentage of the volume of the chamber. This ensures that small volume changes will cause relatively large changes in gas pressure.

The constant $K_V$ will depend on the type of gas used and its temperature. In practice this invention uses atmospheric air from within the processing facility in order to reduce the cost of operation for the system. Preferably, at least one environmental sensor is provided to measuring a quality of the atmospheric air selected, such as humidity, barometric pressure, or any combination and the output of the environmental sensor(s) is used to adjust the calculations and/or modify the process. Alternatively, the entire object measurement mechanism could be enclosed within a climate-controlled housing that maintained a constant temperature and utilized a known mixture of gas. These are precautions that should be considered if the volumes of the objects to be measured are expected to vary across a wide range instead of a more narrow range.

The volumetric measurement system is precise as long as pressure can be precisely determined and the volume of the piston displacement is exactly known. In practice there will be some error in the pressure sensor(s) and some degree of error in the volume change caused by the piston displacement. To overcome these realistic limitations, multiple pistons (or other mechanical or electromechanical displacement mechanism) could be added to the chamber and associated pressure measurements can be made. One skilled in the art can expand the derivation of equation 7 to account for multiple piston movements and associated pressure measurements performed in either a sequential or additive scheme.

Fat Content Determination for Boneless Objects

Precise fat content can be determined for cuts or carcasses that contain fat and lean as well as those that contain fat, lean and bone. The upcoming discussion will cover the fat/lean case, with the bone case being left for later.

Assume we know the precise volume and mass of a cut of meat that contains lean and fat. The mass of the object can be expressed as:

$$M_O = D_F * V_F + D_L * V_L \quad \text{(equation 8)}$$

Where:
 $D_F$=density of fat
 $D_L$=density of lean
 $V_F$=volume of fat
 $V_L$=volume of lean The total volume of the meat can be expressed as the sum of the volume of the fat and the volume of the lean:

$$V_O = V_F + V_L \quad \text{(equation 9)}$$

Combining equations 8 and 9 and solving for $V_F$ or $V_L$ yields:

$$V_F = \frac{M_O - D_L * V_O}{(D_F - D_L)} \quad \text{(equation 10)}$$

$$V_L = \frac{M_O - D_F * V_O}{(D_L - D_F)} \quad \text{(equation 11)}$$

$$\% \text{ fat by volume} = \frac{V_F}{V_O} \quad \text{(equation 12)}$$

Since the density of fat and lean are well known within each particular industry for their products, knowing the precise mass and volume of a cut or carcass allows processors to accurately determine fat content for boneless products.

Fat Content Determination for Boned Objects

Products that contain bones are more difficult, but the problem of determining fat content can be reduced to the case of fat/lean presented earlier. For specific cuts of meat, assumptions can be made about the bone content. For example, a side of beef will contain a discrete number of bones whose mass and volume will correlate to the mass and volume of the side of beef. The volume of bone content can be expressed as:

$$V_B = K_B * V_O \quad \text{(equation 13)}$$

Where:
 $V_B$=volume of bone in an object
 $V_O$=volume of object
 $K_B$=constant representing the % of bone in the object
 $K_B$ will vary according to the type of animal and according to the cut of meat, poultry or fish. In practice, $K_B$ will not be a constant for different sizes of the same cut or carcass. Smaller animals will probably have $K_B$ values that are higher than large animals. For example, two different chickens may have identical volumes, but one chicken may have larger bones. In this case it would be desirable to adjust $K_B$ to account for the larger or smaller boned birds.

One technique is to measure the cross-section of a bone that gives insight into the "largeness" of the bones. If, for example, the diameter of the leg bone of a chicken is a key indicator of the percentage of the chicken volume that contains bone, the bone diameter in the production environment can be measured to determine the $K_B$ value, or the percent of bone. The volume of the boned object is expressed as:

$$V_O = V_F + V_L + V_B \quad \text{(equation 14)}$$

Where:
 $V_O$=volume of object being processed
 $V_F$=volume of fat in an object
 $V_L$=volume of lean in an object
 $V_B$=volume of bone in an object The mass of the boned object can be expressed as:

$$M_O = D_F * V_F + D_L * V_L + D_B * V_B \quad \text{(equation 15)}$$

Where:

$M_O$=mass of object being processed
$D_F$=density of fat in an object
$D_L$=density of lean in an object
$D_B$=density of bone in an object Combining equations 13, 14 and 15 and solving for $V_F$ yields:

$$V_F = \frac{M_O - D_B * K_B * V_O + D_L * V_O * (K_B - 1)}{(D_F - D_L)} \quad \text{(equation 16)}$$

The indicator of $K_B$ for an animal type and cut type can be determined from an exposed section of bone or an encapsulated bone. For exposed bones, non-contact visual techniques can be used to make the precise measurement. For encapsulated bones, X-ray or some other non-visible spectrum radiation and sensor can be used to determine the bone size or thickness. For visible bones, image capture technology using ambient or artificial light can be utilized to produce an image for analysis of bone size. The $K_B$ value for an animal type, cut type and characteristic bone thickness can be determined by an algebraic formula, by values in a lookup table, or any other means of extracting empirical data.

The techniques presented herein allow for the implementation of precise volumetric determination in high-speed production facilities. Implementations of the preferred embodiments can be utilized with throughput as low as one piece per minute and can achieve speeds as high as several thousand pieces per minute.

Preferred Embodiment for Volume Determination— Static Case

FIG. 1 shows a chamber for the precise measurement of volume for a cut of meat. The object to be measured (10) is a whole chicken carcass, although the object could be any comestible food product that has been through the skinning or de-feathering and evisceration stages of a production facility. In one embodiment, the carcass (10), which is suspended from a shackle (40) attached to a conveyor system (30), is placed within an airtight chamber (20) of known volume. The chamber (20) is formed in two sections: the front portion (21), which provides most of the encapsulation of the volume, and the lid (22), which encloses the back of the chamber. Other items that form part of the airtight chamber (20) are the face of the piston (50) and the collar (41) of the shackle (40).

After closure of the airtight chamber (20), the pressure within the chamber is measured with a pressure sensor (70), the value of which is assigned to $P_1$ in equation 7. Next, the piston (50) is engaged via an actuator (60), thus causing the volume within the chamber to decrease. The pressure is measured again with the pressure sensor (70), the value of which is assigned to $P_2$ in equation 7. Using equation 7, a control system or computer processor can determine the precise volume for the object (10) within the chamber (20).

The volume of the chamber (20) in this embodiment will be the volumetric space within the enclosed sections (21, 22) when the piston (50) is in the non-actuated state. The chamber (20) volume will also need to be adjusted for the volume of the shackle (40). For best results the volume within the empty chamber should be determined empirically to account for any variances that occur in the manufacturing of the chamber sections (21,22), the installation of the pressure sensor (70), and the actual position of the non-actuated piston (50). This empirically determined empty chamber volume is assigned to $V_C$ in equation 7.

A control system or module (90) in the form of a programmable logic controller (PLC), microcontroller, microprocessor, computer processor and associated software or hardware control logic and associated firmware performs the measurement of the chamber (20) pressures, calculates whole bird (10) volumes using equation 7, and equates the computed volume to the particular bird (10) number for downstream processing. The pressure within the chamber (20) is transmitted from the pressure sensor (70) to the control module (90) via an interface (75). This interface (75) can be an analog signal medium, a digital electrical medium, a standard electrical interface like Ethernet, Universal Serial Bus (USB), IEEE 1394, an optical transport medium, a wireless connection, or any other mechanism for transporting information between two points.

The control module (90) can also control the actuation of the two sections (21, 22) of the measurement chamber (20) and can control the actuation of the piston (50) via the actuator interface (65). For high-speed production, however, the actuation of the chamber sections (21, 22), the actuation of the piston (50), and the measurement of pressure with the sensor (70) will most likely utilize mechanical methods to decrease the processing burden on the control module (90).

Information regarding the bird (10) tracking number (42) is transmitted to the control module (90) via an interface (80). The information can be in the form of a barcode that is scanned, a numerical indicator on the conveyor line (30), a mechanical counter mechanism, a magnetic strip that is sensed, or a variety of other methods. The interface (80) between the provider of the bird (10) tracking number (42) and the control module (90) can be an analog signal medium, a digital electrical medium, a standard electrical interface like Ethernet, Universal Serial Bus (USB), IEEE 1394, an optical transport medium, a wireless connection, or any other mechanism for transporting information between two points.

Preferred Embodiment for Volume Determination— Dynamic Case

FIG. 2 shows one embodiment of a full production system for the rapid determination of fat content for whole carcasses. The objects shown in FIG. 2 are whole chickens (10) that have been through the de-feathering and evisceration processes. In this embodiment, the birds (10) are each attached to a high-speed, overhead conveyor (30) moving at a constant rate (130). Each bird (10) is connected to the conveyor (30) by a shackle (40). However, it is not essential to the practice of this invention to use an overhead conveyor. Any type of conveyor system including, but not limited to, conveyor belts, bins or buckets that can transport the comestible products through the production assembly could also be used. The only requirement is that the comestible product must at some point be contained within an airtight volumetric determination chamber.

In one embodiment, the birds (10) are first weighed as they pass the scale (100), although other embodiments are possible where the birds (10), or other comestible products, are weighed at a different point in the assembly. Weight information is transmitted to the control module (90) via the scale interface (105).

In one embodiment, after the bird (10) is weighed, an image is taken by an X-ray emitter and collector assembly (110). Other embodiments of the invention could have the X-ray image taken at another point in the assembly or some other form of non-visible radiation emissions could be utilized. The image is transmitted to the control module (90) via the image interface (115). The X-ray image is used to measure an internal image within the bird (10), such as the cross section of one or more encapsulated bones on the bird (10), in order to determine the percentage of the carcass (10) that is bone material. Other embodiments of the present invention may employ visible spectrum, infrared or multi-spectral imaging or other automated, semi-automated or manual process for determining bone length or thickness.

Weighed and imaged birds (10) are next processed by the volumetric determination station (120). This assembly consists of a plurality of receiving chambers (20) that individually encompass each of the moving birds (10) in an airtight compartment (20), measure the initial chamber pressure, decrease the volume by actuating a piston (50), and measuring the resultant pressure. There are five distinct steps executed by the volumetric assembly (120) in the determination of fat content. The stages are driven by mechanical actuators and cams contained within the rotational assembly (120) that rotates at a constant rate (125).

Step one (150) consists of the encapsulation of the bird (10) in an airtight compartment (20) formed by a case (21) and a lid (22), where the lid (22) is a cavity carved into the body of the assembly (120). As the bird (10) rotates past stage one (150), a mechanical cam pushes up the case (21), thereby creating an airtight space (20). Each chamber has a pressure sensor (70) rigidly mounted to the wall of the chamber with externally exposed contacts. In other embodiments of the invention, the sensor (70) can be attached to the lid (22) or the piston (50). The pressure sensor (70) can be comprised of one or more of any number of types of pressure sensors, such as absolute pressure sensors, gauge-type pressure sensors, differential pressure sensors or sealed pressure sensors utilizing such different pressure sensing technologies such as piston measurement, mechanical deflection, strain gauge, semiconductor piezoresistive, piezoelectric, microelectromechanical systems (MEMS), vibrating elements, ultrasonic, solid state or variable capacitance.

Step two (160) consists of the measurement of the initial pressure within the chamber (20). The chamber (20) moves past the pressure measurement assembly (140) and comes in contact with a receiver (145), which allows the chamber pressure data to be transmitted from the pressure measurement assembly (140) to the control module (90) via the pressure interface (141).

In one embodiment, step three (170) utilizes a moving piston (50) to decrease the volume and increase the pressure within the chamber (20). In other embodiments of the invention, the volume could be decreased by a bellow or some other high-speed mechanical or electromechanical device. A mechanical cam is used to actuate the piston (50), which will remain activated until the final pressure measurement is taken. Alternatively, the volume of the chamber (20) could be increased by a moving piston (50) or the like, with appropriate changes made in the calculation of the end result.

Step four (180) consists of the measurement of the final pressure within the chamber. The chamber (20) moves past the pressure measurement assembly (140) and comes in contact with a receiver (146), which allows the chamber pressure data to be transmitted from the pressure measurement assembly (140) to the control module (90) via the pressure interface (141).

Step five (190) is where the two actuation cams are released, thus allowing the piston (50) and the case (21) to return to their original positions.

Upon completion of the processing within the five stages of the rotational assembly (120), the control module (90) has all of the raw information needed to compute the fat content of the bird (10). This raw information consists of a weight, one or more images of internal bone structures, an initial pressure measurement, and a final pressure measurement. These pieces of raw information all need to be associated with the same bird (10).

Several methods exist for maintaining relational timing within a processing facility that gathers product information from different points in time and space. The system described herein works most effectively when the assembly line (30) rate (130) is somewhat constant. A near constant rate allows fewer and lower-cost sensors to be utilized in the synchronization of bird (10) tracking numbers (42) between the various data gathering stations (100, 110, 160, 180, 200). Assembly lines (30) with higher variability in their production rates (130) will require more sophisticated sensors to ensure that the control module (90) can associate the incoming data elements with the appropriate bird (10).

FIG. 2 shows an optional shackle counter (200) that can be used to track the passing of shackles (30). This mechanism utilizes one or more optical sensors to note the movement of shackles (30) past the sensor (200). Multiple sensors (200) may be needed so a non-moving assembly line (30) with a swinging shackle (40) in front of the sensor does not fool the control module (90) into thinking that the assembly line (30) is actually in motion. The sensors (200) can be photo cells, one or more CCD or CMOS cameras, mechanical switches or laser-based switches.

The spacing between shackles (30) is known and will remain a constant for all birds (10). With the known spacing between birds and the periodic shackle counter (200) information being transmitted over the shackle sensor interface (205), the control module can keep track of the assembly line (30) rate (130) at any point in time.

In practice, there will likely be differences in the volumes of the chambers (20) on the processing assembly (120). The volumes of all of the enclosed chambers (20) will need to be determined empirically. Once the volumes are known, it may become necessary to associate pressure measurements with chamber (20) numbers. This problem is easily solved by having an electrical, mechanical, or some other indicator at or near each pressure sensor (70) contact that indicates the chamber (20) number. The chamber (20) number allows the control module to take the actual chamber (20) volume into account when computing the fat content for the bird (10).

The scale (100) weighs the birds (10) as they pass, but equation 16 utilizes the mass of an object. The weight of an object will relate to its mass according to:

$$W_O = g * M_O \qquad \text{(equation 17)}$$

Where:

$W_O$ = weight of an object $M_O$ = mass of an object g = gravitational constant The gravitational constant within the processing facility will be stored in the control module (90) so weight information from the scale (100) can be converted to the mass of the bird (10).

Once the fat content calculation is made for each bird (10), the information can be forwarded to a downstream process to make routing or processing decisions based on the bird's (10) fat content. The control module (90) preferably has a mechanism to communicate the bird (10) tracking number (42) and its associated fat content to this downstream process (210). Several methods exist for communicating this tracking information. One commonly used technique is to have periodic "reference shackles" that carry some characteristic marking (220). These reference shackles can be used to communicate with the downstream process by relating bird (10) tracking numbers (42) relative to a reference shackle (220).

The embodiments shown in FIGS. 1 and 2 utilize a piston (50) that is actuated to cause a volume decrease within the chamber (20). Several other methods can be utilized to decrease volume within the chamber (20) including, but not limited to, bellows, slides, and moving chamber walls. Additionally, the pressure may be changed within the chamber (20) by forcing a known volume of gas into the chamber (20). The volume of gas forced into the chamber (20) would be associated with $V_P$ in equation 16.

The embodiments shown in FIGS. 1 and 2 utilize increasing pressure to compute volume. The system can also utilize decreasing pressure to achieve similar results. Either by removing a known quantity of gas or by increasing the size of the chamber (20), the resulting pressure will be lower than the initial pressure, but the process will still produce accurate volumetric determination.

Determination of the Constant $K_B$

The constant for the percentage of bone in an object ($K_B$) will depend on the type of animal, the cut of meat, the relative size of the cut, and the size of the bones. Each assembly line will be implemented to process a particular cut of meat. The determination of $K_B$ for a cut of meat will begin with the detailed analysis of several representative "samples" for that particular cut. For example, an assembly line has been implemented to determine fat content for sides of beef. Several sides of beef are weighed and subjected to destructive testing to determine their percent of bone content. The statistical results will be used to arrive at values for $K_B$ that relate to the carcass weight.

Two sides of beef with similar weights may contain different bone content due to the "largeness" of the bones. During destructive testing, several bone parameters are measured to determine which bones provide the best indicators for bone content. Statistical analysis will determine the proper bone(s) to be utilized within the factory to indicate values for $K_B$.

In practice the $K_B$ values utilized in fat content determination will be retrieved from a multi-variable lookup table contained within the control module. The variables used for $K_B$ lookup can include, but are not limited to, weight of cut, volume of cut, size of one or more bone cross sections, or the length of one or more bones.

In processing facilities such as those used in poultry production, it is common for whole birds to have missing parts. For example, a turkey with a missing wing will have a different $K_B$ value than a turkey with no missing parts. The system described herein can make determinations about the missing parts and adjust $K_B$ accordingly. The system will need to have empirical knowledge about the various missing parts and how their absence impacts $K_B$. The destructive testing described earlier should account for various missing parts and add the appropriate variables to the multi-variable lookup table for $K_B$.

In extreme circumstances a section of a measured object will be missing that does not correspond to a variable in the $K_B$ lookup table. For example, a chicken may be processed that contains only two legs and a portion of the torso. Since the percentage of the torso remaining does not provide a good indicator of the bone percentage for this partial bird, the system cannot accurately compute the percentage of bone content. In these circumstances the system must be capable of informing the downstream equipment that the fat content determination is not accurate and the partial bird must receive some special handling.

Several of the $K_B$ variables, like bone cross section, bone length and missing part determination require input from two-dimensional sensors. For characteristics that are visible at or above the surface of the cut of meat, visible spectrum digital cameras can be used for image acquisition. For characteristics that lie below the surface of the cut, techniques like X-ray, ultrasonic radiation, or some other form of surface penetrating radiation and detection will be required for image analysis. The determination of missing pieces on a cut and the measurement of bone length or thickness can be performed with imagery from different input sources.

Although it is not practical in high-speed production environments, bone size information, missing parts information or other information necessary to compute $K_B$ could be identified by humans inspecting the cuts of meat as they pass by an inspection station. In this embodiment, manually generated information would be entered into a computer terminal, for example, to associate the particular information to a cut number so the processing system could make the association of the manually supplied information with the proper cut of meat.

Determination of the Constant $K_V$

The constant $K_V$ is utilized to adjust for temperature changes and gas absorption not accounted for in equation 3. Since all cuts of meat will be roughly equivalent in size and will be at the same stage within the production facility, each cut of meat on the line will experience an equivalent temperature increase and gas absorption rate. As a result, the constant $K_V$ will truly be a constant value for a production line with a defined cut of met.

Since cuts of meat come in different sizes and absorb gases differently, each assembly line that processes different animals or different cuts from an animal will have different $K_V$ values. In addition, the size and design of the chamber will impact the $K_V$ value for a given production line.

The value for $K_V$ will likely remain constant throughout a processing shift. Changes from day-to-day, however, can impact $K_V$. For example, humid air will compress differently than dry air. To account for this, it may be necessary to calibrate the $K_V$ value prior to starting a production run. This calibration process could involve placing objects of known volume on the shackles and running them through the volumetric measurement process. The value of $K_V$ could be adjusted so the measured pressure values produce the volumetric result that equals the know volume of the objects.

A more realistic approach for adjusting $K_V$ values for variables like humidity or ambient air temperature would be to provide sensor inputs to the control module that measure the variables that impact $K_V$. The control module could then determine the $K_V$ value by accessing a lookup table that contained pre-determined values for $K_V$ with respect to the known variables.

Other Applications

Although the preferred embodiment of the present invention has been described with respect to meat products, it will be recognized that content analysis of a variety of other kinds of comestible foodstuff products can also be evaluated and determined using the methods and apparatus of the present invention. For example, a watermelon buyer may wish to know the percentage of rind for a batch of watermelons. While it is possible for a buyer to destructively test a few of the melons to determine an estimate of rind content for a given batch of melons, the present invention allows all of the melons to be measured volumetrically and weighed so the precise rind content for each melon would be known. The melon buyer could use this information to determine the price to pay the grower and could assign grades to each melon in order to maximize the profit margin of the product sold to consumers.

As another example, assume that a bread manufacturer purchases wheat directly from growers, but utilizes only wheat hearts in the production of bread. The manufacturer could pay the grower based on the percentage of wheat hearts or the actual weight of wheat hearts contained within a shipment of wheat. In this example the bread manufacturer would use the known densities of wheat hearts and wheat chaff to determine heart content.

Yet another example would be to determine the volume of flavored chips in processed cookies. By measuring the weight and volume of finished cookies and knowing the densities of the cookie and chips, the percent of chips by volume or weight can be determined for the finished product. The cookie manufacturer could use this information to sort cookies into their percent chip categories or could be used as a quality control check for the mixing and baking process.

The above description has been of preferred embodiments of the present invention and one skilled in the art will realize that numerous modifications may be made without departing from the spirit and scope of the invention.

What is claimed is:

1. A device for rapidly determining a content value of a plurality of comestible products comprising:
   a conveyer system that transports the plurality of comestible products along a path;
   means for detecting a weight of each of the plurality of comestible products;
   a plurality of individual volumetric measurement chambers operably coupled to the path of the conveyer system, each chamber dimensioned to accommodate one of the plurality of comestible products and arranged to define a space that is selectively sealable upon introduction of the one of the plurality of comestible products into the space;
   means for modifying the volume by a known amount for each of the plurality of individual volumetric measurement chambers;
   means for detecting a change in a pressure in the space of each chamber while one of the plurality of comestible products is in the space; and
   control means operably connected to the conveyer system, the means for weighing, the means for modifying the volume by a known amount and the means for detecting the change in pressure for controlling operation of the device so as to determine a content value for each of the plurality of comestible products based on the change in pressure, the known change in volume and the weight associated with that comestible product.

2. The device of claim 1, wherein the content value is selected from the set consisting of: a percentage fat content, a percentage lean content, or both.

3. The device of claim 1, wherein the conveyor system is a high-speed overhead conveyor moving at a constant rate.

4. The device of claim 3, wherein the conveyor system includes shackles that connect the comestible products to the overhead conveyor and means for tracking the shackles moving along the path of the conveyor.

5. The device of claim 4, wherein the means for tracking the shackles is a shackle counter that utilizes one or more optical sensors to track the shackles.

6. The device of claim 1, further comprising a radiation emitter and collector assembly that takes images of the comestible products as the comestible products are transported along the path of the conveyor.

7. The device of claim 6, wherein the image taken by the collector is transmitted to the control module via an image interface.

8. The device of claim 1, further comprising a radiation collector assembly that collects images of the comestible product as the comestible products are transported along the path of the conveyor.

9. The device of claim 1, wherein the comestible product is a meat product and where the device further comprises means for providing information about bone content within the meat product.

10. The device of claim 1, wherein the means for modifying the volume by a known amount for each of the plurality of individual volumetric measurement chambers is a piston.

11. The device of claim 1, wherein the means for modifying the volume by a known amount for each of the plurality of individual volumetric measurement chambers comprises multiple pistons.

12. The device of claim 1, wherein each of the plurality of chambers is assigned a tracking number and wherein the tracking number is provided to the control means in connection with the change in pressure for a given chamber.

13. The device of claim 1, wherein ambient air is used within each of the plurality of chambers and further comprising at least one environmental sensor operably coupled to the control means for measuring a quality of the ambient air selected from the set consisting of:
   temperature, humidity, barometric pressure, or any combination thereof.

14. An automated method for rapidly determining a content value of a plurality of comestible products comprising the steps of:
   using a conveyor to move the comestible products along a path of the conveyor,
   weighing the comestible products;
   enclosing each comestible product individually into one of a plurality of volumetric receiving chambers that are operably coupled to the path of the conveyor system, each volumetric receiving chamber having a known volume;
   determining an initial pressure inside each of the plurality of volumetric measurement chambers;
   modifying the volume of each of the plurality of volumetric receiving chambers;
   determining a final pressure in each of the plurality of volumetric receiving chambers after the volume of each chamber has been modified; and
   determining a volume based upon the known modified volume of the chamber associated with a given comestible product chamber, the initial pressure and the final pressure; and
   using the volume and weight of the comestible product to determine a content value.

15. The method of claim 14, wherein the content value is selected from the set consisting of: a percentage fat content, a percentage lean content, or both.

16. The method of claim 14, further comprising tracking the comestible products along the path of the conveyor so that a comestible product can be matched to a particular content value.

17. The method of claim 14, wherein the comestible product is a meat product and wherein the method further comprises: providing information about at least one internal bone structure to allow determination of a percentage bone content of the comestible product.

* * * * *